(12) United States Patent
Johnson

(10) Patent No.: US 8,714,976 B2
(45) Date of Patent: May 6, 2014

(54) FATIGUE-RESISTANT NITINOL INSTRUMENT

(76) Inventor: William B. Johnson, Tulsa, OK (US)

(*) Notice: Subject to any disclaimer, the term of this patent is extended or adjusted under 35 U.S.C. 154(b) by 0 days.

(21) Appl. No.: 13/510,500

(22) PCT Filed: Nov. 17, 2010

(86) PCT No.: PCT/US2010/056999
§ 371 (c)(1),
(2), (4) Date: May 17, 2012

(87) PCT Pub. No.: WO2011/062970
PCT Pub. Date: May 26, 2011

(65) Prior Publication Data
US 2012/0231414 A1    Sep. 13, 2012

Related U.S. Application Data

(60) Provisional application No. 61/262,008, filed on Nov. 17, 2009.

(51) Int. Cl.
*A61C 5/02* (2006.01)
(52) U.S. Cl.
USPC .......................................... 433/102; 433/224
(58) Field of Classification Search
USPC ................................................ 433/102, 224
See application file for complete search history.

(56) References Cited

U.S. PATENT DOCUMENTS

| | | | | |
|---|---|---|---|---|
| 4,283,233 A | * | 8/1981 | Goldstein et al. | 148/563 |
| 4,336,312 A | | 6/1982 | Clark | |
| 5,318,527 A | * | 6/1994 | Hyde et al. | 604/95.04 |
| 5,624,508 A | * | 4/1997 | Flomenblit et al. | 148/510 |
| 5,931,819 A | * | 8/1999 | Fariabi | 604/525 |
| 2006/0115786 A1 | * | 6/2006 | Matsutani et al. | 433/102 |
| 2007/0072147 A1 | | 3/2007 | Berendt | |

OTHER PUBLICATIONS

Nayan et al, Effect of mecanical cycling on the stress-strain response of a martensitic Nitinol shape memory alloy, Materials Science & Engineering (Nov. 15, 2009) vol. 525.

* cited by examiner

*Primary Examiner* — Ralph Lewis
(74) *Attorney, Agent, or Firm* — Gable Gotwals

(57) ABSTRACT

A fatigue-resistant Nitinol instrument has a working portion in the deformed monoclinic martensitic state and an austenite finish temperature in the range of 40° to 60° C. Because the operating environment of the instrument is about 37° C., the working portion remains in the monoclinic martensitic state during its use. The relatively high austenite finish temperature and fatigue resistance is achieved by subjecting the nickel-titanium alloy to a final thermal heat treat in a temperature range of about 410° to 440° C. while the nickel-titanium alloy is under constant strain of about 3 to 15 kg. Further, the high austenite finish temperature is achieved without subjecting the alloy to thermal cycling to produce shape memory. Additionally, there are no intermediate processing steps occurring between obtaining a finished diameter of the wire or blank through cold working and the final thermal heat treat under constant strain.

16 Claims, 6 Drawing Sheets

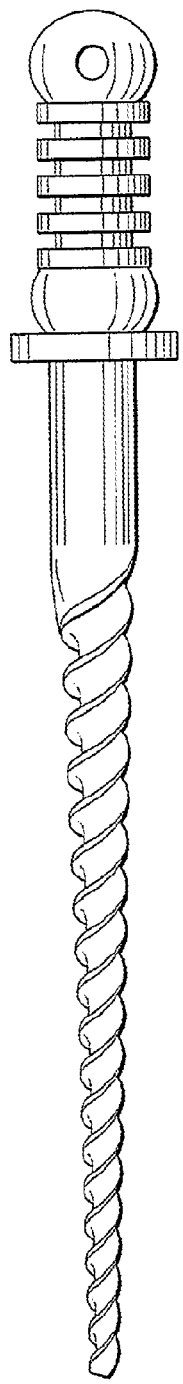 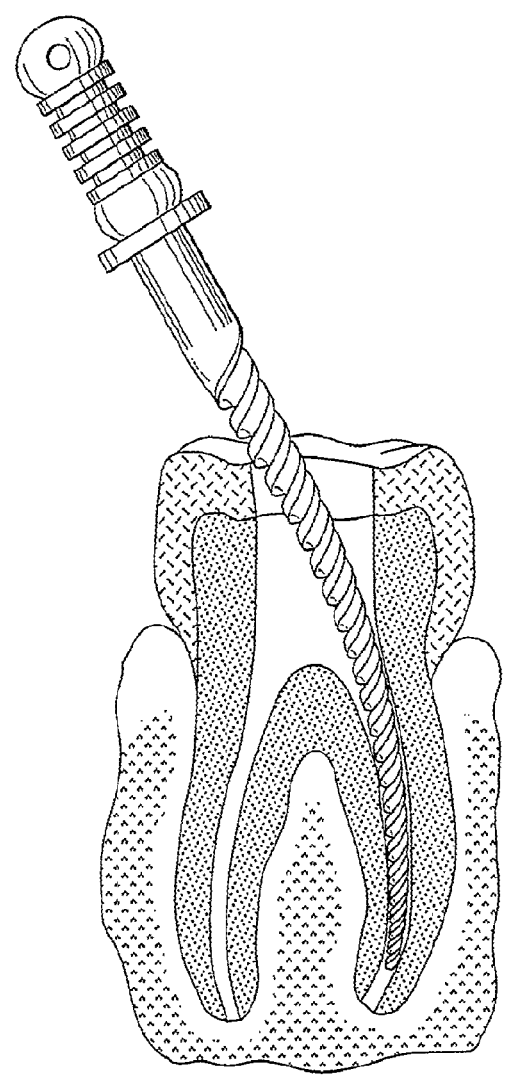
Fig. 1
Fig. 2

FATIGUE-RESISTANT NITINOL INSTRUMENT

CROSS-REFERENCE TO PENDING APPLICATIONS

This application claims priority to, and the benefit of, U.S. Provisional Pat. App. No. 61/262,008, filed Nov. 17, 2009.

BACKGROUND

The present invention is related generally to a method of treating a nickel titanium alloy, known as Nitinol, for use in manufacturing instruments having improved resistance to cyclic fatigue failure. As a particular application, the invention is related to preparation of Nitinol wire blanks for use in manufacturing instruments for use in the human body having improved resistance to cyclic fatigue failures.

Many medical applications take advantage of the properties of Nitinol, a nickel and titanium alloy. Nitinol (an acronym for Nickel Titanium Naval Ordinance Laboratory) exhibits several useful properties such as shape memory, by which a Nitinol component returns to a previously memorized shape after being forced into a second shape. Nitinol also exhibits superelasticity, meaning that a Nitinol component may be deformed elastically to a very large extent by strain without reducing its ability to return to its original shape after the strain has been removed. Nitinol is very flexible and resistant to cyclic fatigue when compared to stainless steel, which makes Nitinol the material of choice in medical and dental applications. However, cyclic fatigue remains a common problem with Nitinol medical and dental instruments. For example, Shen et al. compared the incidence and mode of instrument separation of two Nitinol rotary systems, ProFile and ProTaper. A total of 166 ProFile and 325 ProTaper instruments—which were used according to a pre-defined schedule of clinical use by the same group of operators—was analyzed. Flexural fatigue was implicated in the majority of separations in both groups, with 66% of the separated ProFile instruments and 95% of the ProTaper instruments fracturing because of cyclic fatigue. See Ya Shen et al., *Comparison of Defects in ProFile and ProTaper Systems after Clinical Use*, 32 J. Endodontics 61 (No. 1, January 2006).

As would be understood by those of skill in the art, Nitinol alloys can exist in one of two different temperature-dependent crystal structures—austenite at higher temperatures and martensite at lower temperatures—and within a given temperature range, the alloy can stabilize as one or the other. In general terms this temperature-dependent phase transformation is from martensite to austenite during heating, while the reverse transformation from austenite to martensite starts upon cooling. As the temperature increases above a certain critical temperature, known as the austenite start temperature or $A_S$, the alloy rapidly changes in composition between the martensite and austenite form and completes the transition to austenite at a critical temperature known as the austenite finish temperature or $A_F$.

There are two known methods for obtaining a target $A_F$ temperature: varying the nickel-to-titanium ratio and thermally heat treating the material at its finished form. The $A_F$ of Nitinol is affected directly by the ratio of nickel to titanium during production of the ingot. The target $A_F$ temperature can be lowered or raised by varying the nickel percentage alone. The $A_F$ temperature is also directly affected by the processing of the material post-ingot form by the amount of cold work, the temperatures at which the material is thermally heat treated, and the amount of strain induced during processing. Therefore, a target $A_F$ is achievable by varying the nickel percentage, the thermal heat treat process of the material, or both accordingly.

Because Nitinol in the martensite form is soft and malleable, it demonstrates improved fatigue resistance, which is due to the differing crystalline structures between Nitinol in its martensitic and austenitic state. Austenitic Nitinol's crystalline structure is known to be that of a face centered cubic lattice, while the martensitic crystalline structure is that of a monoclinic distorted structure with atomic dislocations.

The distorted structure of martensitic Nitinol allows for the material to be deformed at greater angles and working conditions than that of the austenitic Nitinol in those same angles or working conditions. Generally, when the working or working environment is above the $A_F$ temperature, meaning the Nitinol is in its austenitic state, the material cannot withstand the same level of stress/strain—such as cyclical fatigue—as it can withstand when it is below the $A_F$ temperature and transitioning to (or transitioned into) its martensitic state. Nitinol in the austenite form is strong and hard, having a much more regular crystalline lattice structure and exhibiting properties similar to those of titanium. In the field of endodontic instruments, conventional wisdom holds that Nitinol must be primarily in its austenitic state in order to provide required stiffness and strength.

Nitinol alloys can also undergo a phase change between austenite and martensite as a result of the application of a strain. Therefore, a strain-induced martensite can exist in the alloy at temperatures up to a martensitic deformation temperature $M_D$, which is typically above the austenite finish temperature $A_F$. For example, Nitinol in the austenitic phase can be bent so that at high strain locations the alloy becomes martensitic. If the alloy is designed to have an unstable martensite phase at its intended application's operating temperature, removal of the strain results in a reverse transformation that straightens the bending. This reverse transformation is an example of what is known as shape memory and is considered an essential feature of Nitinol.

The prior art teaches a process by which Nitinol in its martensitic state undergoes cold and hot cycling to stabilize the martensitic twins and therefore significantly improve fatigue performance (see U.S. Pat. No. 7,648,599 to Berendt, titled "Method of Preparing Nickel Titanium Alloy for Use in Manufacturing Instruments with Improved Fatigue Resistance.") This cycling process works to stabilize the crystalline structure of the Nitinol in its more martensitic condition and maintains the stabilized martensitic twins for long term usage.

Subsequent testing has shown that this hot and cold cycling is not necessary to achieve a level of improved fatigue performance sufficient for medical and dental instruments, which typically are single use instruments. In other words, it is not necessary to provide the stabilized martensitic twins because the fatigue resistance provided by the twins is well beyond the amount of cycling encountered during a medical and dental instrument's single use. Further, it is not necessary to provide the shape memory feature. Shape memory is not a desired feature in instruments rotating around a curve or being placed in a curve because the shape memory is a restorative force. As the instrument attempts to straighten itself, it can damage the surrounding tissue (e.g., an arterial wall or a tooth root canal).

Last, in the process of finishing a Nitinol medical instrument, machining operations such as grinding may be employed. These machining operations degrade the physical properties of the material. For example, prior to machining operations a Nitinol wire prepared using the method of U.S. Pat. No. 7,648,599 might be five-times more resistant to cyclic fatigue than Nitinol wires prepared by conventional means. After machining operations, this same wire might be only three-times more resistant. The machining processes produce mechanical stress and frictional heat which alter the characteristics of the surface of wire.

SUMMARY OF THE INVENTION

A fatigue-resistant Nitinol material made according to this invention has a working portion composed of a nickel-titanium alloy and configured for use in the human body. The working portion is in the deformed monoclinic martensitic state and has an austenite finish temperature in the range of 30 to 60° C. Because the operating environment of the instrument is about 37° C., the working portion remains in the monoclinic martensitic state during its use.

The relatively high austenite finish temperature and fatigue resistance is achieved by subjecting the nickel-titanium alloy to a final thermal heat treat in a temperature range of about 410 to 440° C. while the nickel-titanium alloy is under constant strain. The constant strain is caused by placing the heated alloy in tension in a range of about 3 to 15 kg. Further, the high austenite finish temperature is achieved without subjecting the alloy to thermal cycling to produce shape memory. Additionally, there are no intermediate processing steps occurring between obtaining a finished diameter of the wire or blank through cold working and the final thermal heat treat under constant strain.

The alloy's material characteristics are accomplished with fewer process steps than prior art processes. One such prior-art process subjects the alloy to thermal cycling while the alloy is subjected to strain. The cold bath of the thermal cycle is in a temperature range of about 0° to 10° C. and the hot bath is in a temperature range of 100° to 180° C.

Objects of this invention are to produce a Nitinol material that is suitable for use in the human body (or in other applications) and (1) has an austenitic finish temperature well above that of the normal operating temperature of the instrument; (2) can be subjected to cyclic fatigue; (3) can traverse a bend or curve; (4) can rotate around a bend or curve in excess of 90 degrees; (5) retains the martensitic state, and in particular the monoclinic martensitic state, within the expected operating temperature range of the instrument; (6) has improved resistance to cyclic fatigue with significantly fewer process steps than current methods; (7) has reduced shape memory properties; and (8) does not require or rely upon shape memory properties.

BRIEF DESCRIPTION OF THE DRAWINGS

FIG. 1 is an elevational view of an endodontic instrument or file. The endodontic file is one example of a medical device that can be successfully manufactured by employing Nitinol material which is made according to the present invention.

FIG. 2 is an elevational cross-sectional view of a human molar, its root canal system and the coronal area penetrated by a hole to expose the root canal system. The endodontic file of FIG. 1, when positioned within the root canal, is subjected to substantial bending and torsional stress as it cleans and shapes the root canal. A Nitinol material made according to the present invention significantly increases the file's resistance to cyclic fatigue.

DETAILED DESCRIPTION OF THE PREFERRED EMBODIMENTS

The starting material for use in an apparatus and method practiced according to this invention is a Nitinol composition consisting of preferably 55.8+/−1.5 wt. % nickel (Ni), with the balance being that of titanium (Ti). There are also trace elements including iron (Fe), chromium (Cr), copper (Cu), cobalt (Co), oxygen (O), hydrogen (H), and/or carbon (C), generally less than 1 wt. % each. The Nitinol composition may also consist of 50+/−10 wt. % nickel, with the balance being that of titanium and the trace elements.

Figure 3:
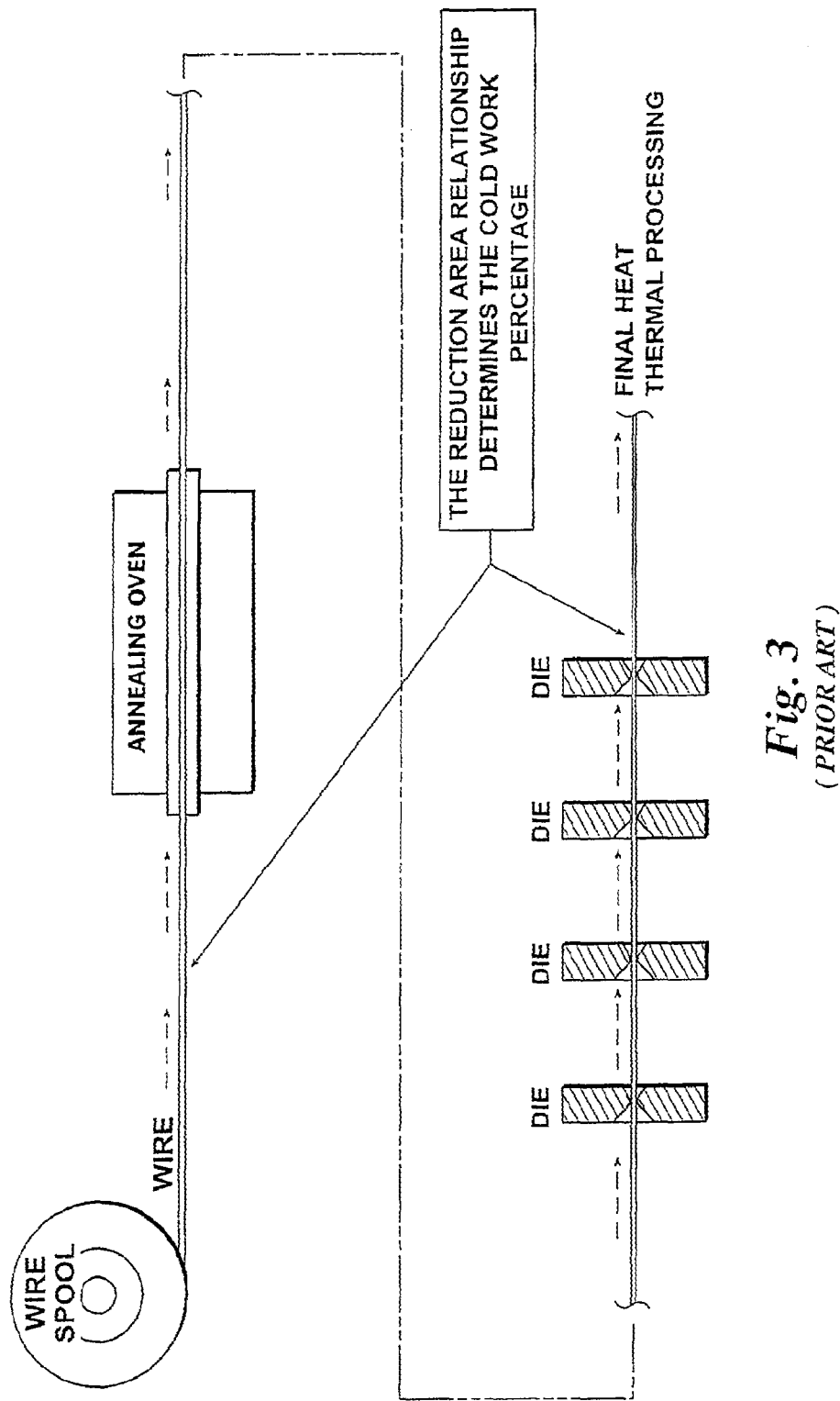
FIG. 3 illustrates prior art cold working procedures that can be employed in preparing Nitinol wire for the prior art final manufacturing steps as shown in FIG. 4 or the steps of the present invention as shown in FIG. 8.

Referring first to FIG. 3, a prior-art process shows the steps normally employed to convert a Nitinol wire into a stable martensite state useable for manufacturing fatigue resistant devices. One example of this type of device is the endodontic instrument illustrated in FIGS. 1 and 2. In the prior art process, untreated Nitinol wire is unwound from a spool and passed through an annealing oven, a series of dies, and final heat thermal processing operation. The temperatures used and the amount of cold working depend upon such factors as the amount of stiffness (or, conversely, flexibility) desired in the wire and the diameter of the wire. Typically, the cold working step achieves about a 45+/−10% reduction in cross-sectional area of the wire and is followed by final heat thermal processing at about 500° to 800° C. (930° to 1475° F.) for a time period sufficient to anneal the wire based upon its diameter. The process according to the present invention may be preceded by these cold working steps but eliminates the need for the high temperature anneal of FIG. 3.

Figure 4:
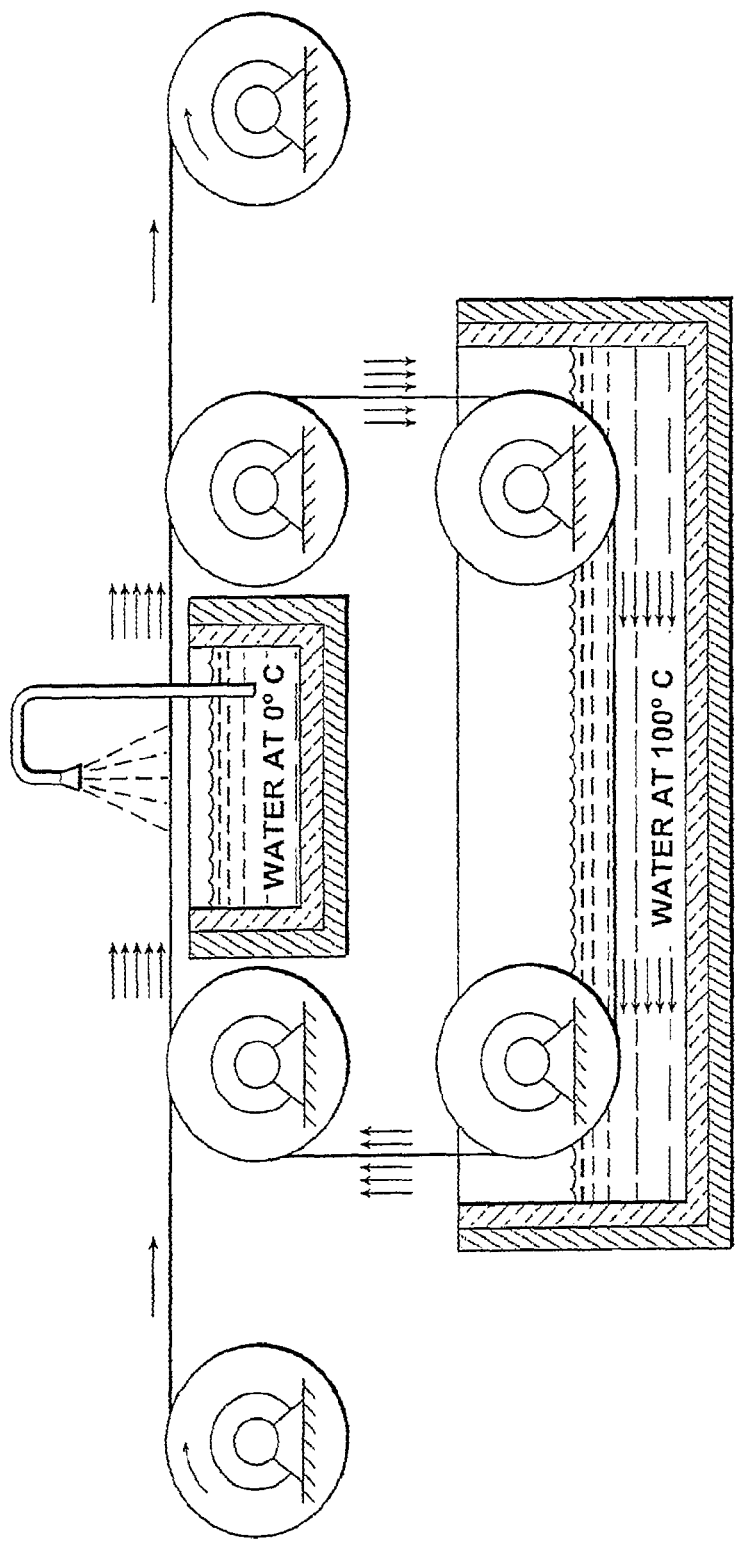
FIG. 4 is a diagrammatic illustration of steps employed in a prior art process to treat the Nitinol wire of FIG. 3 so that it can be employed for producing instruments having greatly improved resistance to cyclic fatigue. The present invention eliminates the need for the steps of FIG. 4.

Another prior art process—disclosed in U.S. Pat. No. 7,648,599—subjects the Nitinol wire from FIG. 3 to a "micro-twining and de-twinning" process (also known as a "training" process). FIG. 4 shows the steps of the training process. The Nitinol wire is placed under a constant 1 to 10% elongation or strain as it is repeatedly thermal cycled between a cold and hot bath. The cold bath is at a temperature in the range of about 0 to 10° C. (32° to 50° F.) and the hot bath is in the range of about 100 to 180° C. (212° to 356° F.). As a result, the micro-twinning structure undergoes a de-twinning or realignment process to achieve an energetically stable martensitic structure with reduced interfacial friction and residual deformation. This contributes to the improved fatigue resistance of the Nitinol wire which results from this process.

Figure 5:
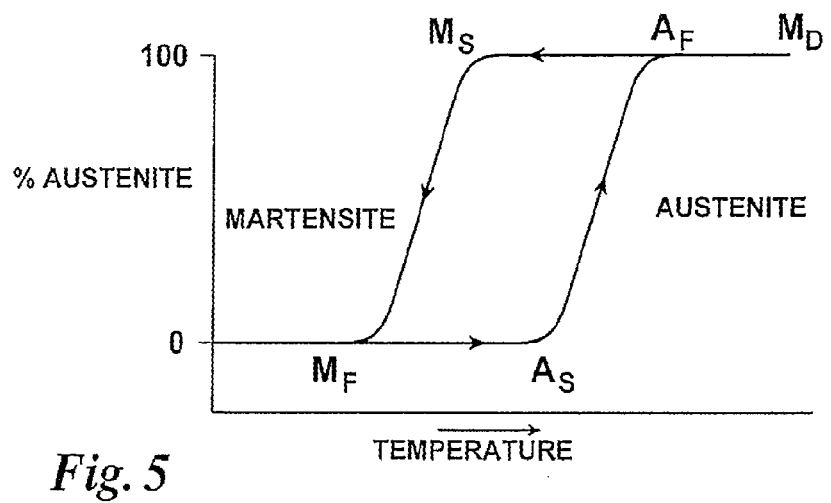
FIG. 5 is a graph illustrating the hysteresis effect as Nitinol is transitioned between martensite and austenite phases.

Nitinol as an alloy exists in two naturally occurring forms, that is, in the austenite form and in the martensite form. The alloy transitions between martensite and austenite, and can stabilize as either martensite or austenite, within a given temperature range (see FIG. 5). The austenite phase in the alloy is plotted as a function of the temperature, with several important transition temperatures marked. $A_S$ indicates the temperature at which the austenite starts and $A_F$ indicates the temperature at which the alloy is 100% in the austenite phase. $M_S$ and $M_F$ indicate the martensite start and finish temperatures, respectively. Starting with Nitinol in its martensitic state at temperature $M_F$ and increasing the temperature above $M_F$ to $A_S$, the austenite form begins. As the temperature continues to increase above $A_S$, the austenite form increases as a percent of the alloy until the temperature reaches $A_F$. The alloy will remain in the 100% austenite form at temperatures at or above $A_F$.

Note the austenite and martensite phase transformations do not occur at the same temperature. Rather, a hysteresis loop exists corresponding to the phase transformation. In addition, a $M_D$ temperature exists. The $M_D$ temperature is the highest temperature at which strain-induced martensite can exist, i.e., the temperature above which martensite cannot be induced by strain. (The terms, strain, elongation, tension, stress and deformation are used interchangeably in this context.) Nitinol in the martensite form can demonstrate significantly improved fatigue resistance relative to Nitinol in the austenite form.

As would be understood by those skilled in the art, the specific temperatures at which Nitinol transitions occur are very sensitive to small variations in the alloy's content of nickel, titanium and any other trace elements. Therefore, Nitinol's properties can be tailored for specific applications by controlling the alloy's composition.

Figure 6:
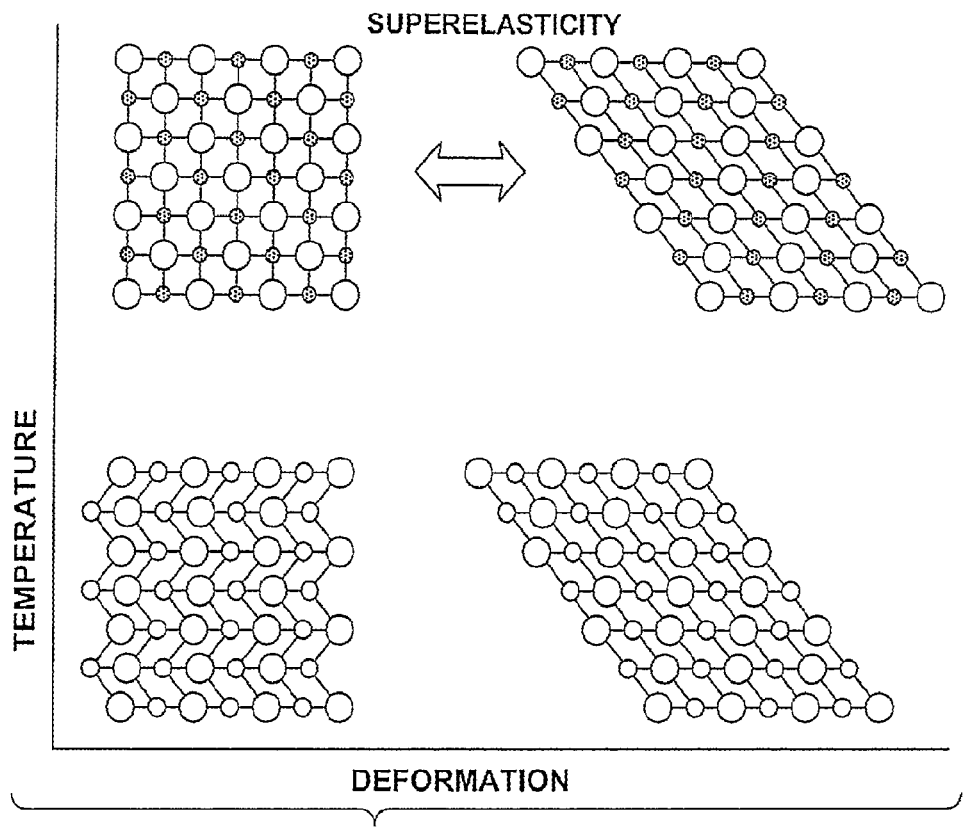
FIG. 6 illustrates diagrammatically the transitions of Nitinol between austenite and martensite phases in response to changes in temperature and deformation.

FIG. 6 pictorially illustrates the transition of Nitinol between the austenite form and the martensite form. The nickel is illustrated by the large non-shaded circles. The titanium is illustrated by the small shaded circles. When the alloy is in the austenite state, the arrangement of atoms is orderly. As the temperature of the alloy cools, the atomic structure changes from the initial orderly structure to a twinned martensite arrangement or state. In this twinned martensite state, and without a significant change in temperature, the alloy can be subjected to strain in order to transform into "deformed martensite" or "de-twinned martensite" state. The alloy can remain in this state until heat is applied to reach the level of the austenite start ($A_S$). As further heat is applied the alloy returns to the 100% austenite state ($A_F$).

Figure 7:
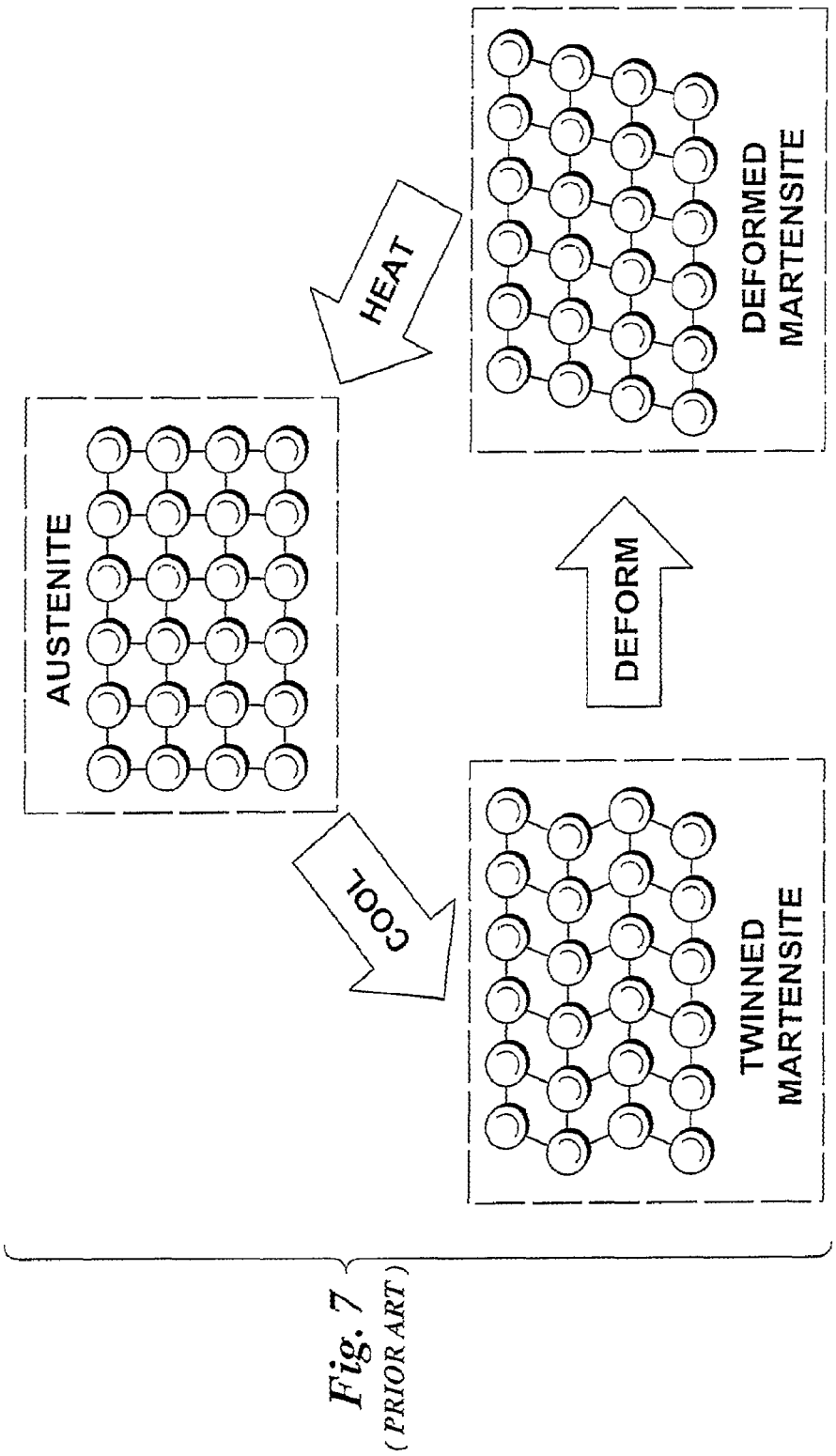
FIG. 7 shows diagrammatically the changes in phases of Nitinol in response to changes in temperature and stress as is shown in FIG. 6, but in somewhat greater detail, as the Nitinol is subjected to the prior art process of FIG. 4.

The shape memory and superelastic properties of Nitinol may be understood in terms of the phase transformations the alloy undergoes under various conditions. Shape memory refers to the ability to restore an originally memorized shape of a deformed Nitinol sample by heating it. Referring to FIG. 7, the alloy is heated to a temperature above $A_F$ and, when in the austenite state, formed into a desired shape. This causes the alloy to memorize the desired shape. Lowering the temperature below $M_S$, moves the alloy into the twinned martensite state. If a deformation-inducing strain is applied to the alloy when in this state, the alloy will move to the deformed martensite state and will retain that shape even after the strain has been removed. Then, if the alloy is again heated to a temperature above $A_F$, a thermo-elastic phase transformation takes place. The element returns to its previously memorized austenite shape, thereby regaining its strength and rigidity.

As mentioned previously, the present invention does not require the high temperature, final thermal heat processing of FIG. 3 (after cold working), nor does it require the training process of FIG. 4, in order to achieve a martensitic structure that produces superior and unexpected fatigue performance. Unlike these prior art processes, the Nitinol material here is subjected to final thermal heat treat at about 410° to 440° C. (770° to 824° F.) while being subjected to a preferably constant strain of in the range of about 3 to 15 kg (see FIG. 8).

Figure 8:
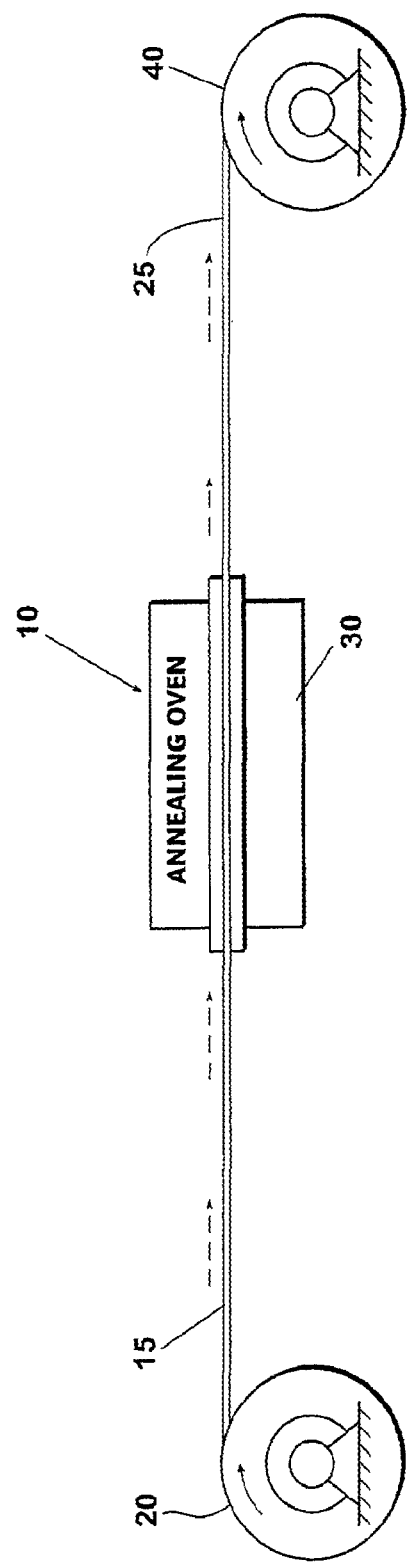
FIG. 8 is a diagrammatic illustration of steps employed in the present invention. These steps may follow the cold working steps illustrated in FIG. 3. The steps of FIG. 8 eliminate the need for processing steps similar to or the same as those illustrated in FIG. 4 or those required to produce shape memory properties. After machining operations, the finished instrument may be subjected to a finished instrument heat treat to counteract any degradation that may have occurred to fatigue performance due to machining and restore and enhance the fatigue characteristics achieved by the process of FIG. 8.

In a preferred embodiment, wire 15 that has been cold worked (see FIG. 3) is passed through an oven 30 for final thermal heat treat while under strain (FIG. 8). Wire 15 going out of the cold working process may be passed directly to over 30 or first wound about a spool 20. Wire 15 wound about spool 20 could also be supplied by a manufacturer of Nitinol alloy products and already cold worked to the desired dimension for subsequent machining operations. The treated wire 25 may be wound about a finish spool 30. Wire 25 is in condition to be used to manufacture products, specifically instrumentation or other products that require a high degree of flexibility combined with an unusually high fatigue resistance characteristic and high austenite finish temperature.

The resultant Nitinol material or wire 25 is in a transitory martensitic state (i.e. in the deformed monoclinic state) and has the following properties:

| Properties | |
|---|---|
| Austenitic finish temperature $A_F$ (° C.) | ~30-60 |
| Ultimate tensile strength | >200 Ksi |
| Permanent set (PS @ 7 Mpa) | 20 |
| Ultimate tensile strength to upper plateau stress ratio | ~2.5 |

A person of ordinary skill in the art understands that the $A_F$ is very sensitive to changes in nickel composition and, therefore, to hold the $A_F$ at a desired level, the nickel composition must be held steady for any manufacturing process to achieve a repeatable $A_F$. For example, the estimated percentage of nickel to accomplish an $A_F$ of about 50° C. (122° F.) using the process of FIG. 8 would be approximately 55.3%. Therefore, the percentage of nickel used to achieve a desired $A_F$ by way of the above method may be altered as appropriate.

Endodontic instruments (see FIGS. 1 & 2) made using Nitinol wire which was prepared according to this method (FIG. 8) were tested at room temperature in a rotary system along a 90° curve. The instruments averaged about 11 minutes to failure. Instruments made according to the prior art training process of FIG. 4 averaged about 2.3 minutes to failure (still far above that of instruments made only according to the process of FIG. 3).

The instruments also exhibited reduced shape memory. Shape memory is not an asset for any instrument which must traverse a curve or be positioned within a curve because shape memory is a restoring force. To test the shape memory properties of an instrument made according to the process of FIG. 8, the instrument was placed in a fixture and bent at a 90° angle and released. This bend and release was repeated two more times. An instrument without any shape memory will remain bent at 90° once released. Typically, a Nitinol instrument with shape memory properties exhibits about 88° of restoration. That is, after being bent 90°, the instrument returns to a position about 2° less than its original starting position. In other words, instead of traveling a full 180° (90° bend, 90° return), the instrument travels about 178° total.

A Nitinol instrument made according to the process of FIG. 4 is typically in the range of about 10° to 15° off of straight after the repeated bend-and-release test (exhibiting roughly 165° to 170° of total travel). The shape memory restorative property is in the range of about 80 to 90 percent.

Instruments made according to FIG. 8 exhibited even less shape memory than those made according to FIG. 4, being about 25° to 35° off of straight after repeated bend-and-release (roughly 145° to 155° of total travel). Therefore, the shape memory restorative property of the instrument is about 60 to 75 percent.

The medical or dental instrument provided by the method of FIG. 8 (and by the method of FIGS. 3 and 4) typically undergoes subsequent machining operations to produce the desired final instrument. For example, grinding operations may produce the helical flutes and cutting edges of the endodontic instruments of FIGS. 1 and 2. Because of mechanical deformation and frictional heat caused by the grinding, the fatigue performance of the instrument is negatively affected. Putting the final machined instrument through a finished instrument heat treat in a temperature range of about 248 to 500° C. (478 to 932° F.) restores and can enhance the fatigue-resistant properties of the instrument, with heat treat in the range of 350 to 450° C. (662 to 842° F.) being best. A longer time is required for heat treat at the lower end of this temperature range and a shorter time is required for heat treat at the higher end.

Producing an instrument according to the process of FIG. 8 reduces the restoring force by about half when compared to the process of FIG. 8. Subjecting the finished instrument to a final instrument heat treat produces even less restoring force but with improved resistance to cyclic fatigue with minimal or insignificant loss in torque performance.

An austenitic finish temperature $A_F$ above 37° C. is important for instruments adapted for use in the human body than is the stabilized martensitic effect and shape memory achieved by the prior art process of FIG. 4. Additionally, an $A_F$ above 37° C. may be achieved by eliminating the strain-induced thermal cycling steps of FIG. 4 and simply subjecting the Nitinol to a strain-induced final straightening thermal heat treat in the range of 410° to 440° C., varying the nickel percentage at the ingot level, or applying both strain-induced heat treat and varying the nickel percentage. This results in a Nitinol alloy with significant resistance to cyclic fatigue but without requiring the additional processing steps and elevated temperatures of prior art processes. Further, the alloy has a high $A_F$. To date, no manufacturer of endodontic instruments produces an instrument in which the Nitinol is in a martensitic or transitory state (i.e. in the deformed monoclinic state) and having a high $A_F$.

While preferred embodiments of a Nitinol instrument made according to this invention have been described in enough detail for those of ordinary skill in the art, changes can be made to it without departing from the scope of this disclosure. Therefore, the present invention is only limited by the following claims, including equivalents to the individually recited requirements of each claim.

What is claimed is:

1. An endodontic instrument comprising:
    a working portion composed of a nickel-titanium alloy and configured for use in the human body, the working portion having an austenite finish temperature in the range of 40 to 60° C. and being in a deformed monoclinic martensitic state and having, after a 90° bend and release, a shape memory in a range of 60 to 75 percent of the 90° bend,
    wherein the austenite finish temperature, the deformed monoclinic state, and the shape memory restoration are a result of a final thermal heat treat of the working portion before machining while the nickel-titanium alloy is under constant strain and a finished instrument thermal heat treat of the working portion after machining.

2. An endodontic instrument according to claim 1 further comprising the final thermal heat treat of the working portion before machining while the nickel titanium alloy is under constant strain being in a temperature range of about 410 to 440° C.

3. An endodontic instrument according to claim 2 further comprising the constant strain being caused by a load in a range of 3 to 15 kg.

4. An endodontic instrument according to claim 1 further comprising the shape memory restoration being achieved without subjecting the nickel-titanium alloy to thermal cycling to produce shape memory.

5. An endodontic instrument according to claim 1 further comprising the shape memory restoration being achieved without thermal cycling the nickel-titanium alloy while under constant strain after cold working.

6. A high fatigue-life endodontic wire comprising:
    a nickel-titanium alloy material having a composition of about 50±10 wt. % nickel (Ni) with a balance of titanium (Ti) and trace elements, the trace elements being about 1 wt. %;
    the high fatigue-life endodontic wire when in a finished state being in a deformed monoclinic martensitic state and having an austenite finish temperature in the range of 40 to 60° C. as a result of cold working the nickel-titanium alloy material, final thermal heat treating the cold-worked nickel titanium alloy material while under constant strain, and heat treating the nickel-titanium alloy material when in a finished instrument state.

7. A high fatigue-life endodontic wire according to claim 6 further comprising the high fatigue-life wire undergoing the final thermal heat treat in a temperature range of about 410 to 440° C., there being no intermediate processing steps occurring between cold working the high-fatigue-life endodontic and the final thermal heat treat.

8. A high fatigue-life endodontic wire according to claim 7 further comprising the constant strain being caused by a load in a range of 3 to 15 kg.

9. A high fatigue-life endodontic wire according to claim 7 further comprising the nickel content of the high fatigue-life endodontic wire being in a range of 54.3 to 57.3 wt. %.

10. A high fatigue-life endodontic wire according to claim 7 further comprising the high fatigue-life endodontic wire being final cold worked in a range of about 35 to 45% to a finished diameter prior to machining operations, the final cold work occurring prior to the final thermal heat treat.

11. A method of manufacturing an endodontic instrument from a nickel-titanium blank to obtain improved fatigue failure characteristics, the method comprising the steps of:
    (i) applying an elongational strain deformation to the blank within its reversible strain limit at a temperature of about 410 to 440° C.;
    (ii) after step (i), forming an instrument from the blank by performing machining operations; and
    (iii) after step (ii), heat treating the instrument.

12. A method according to claim 11 further comprising the elongational strain deformation resulting from a strain caused by a load in a range of 3 to 15 kg.

13. A method according to claim 11 further comprising the instrument after the step (iii) heat treat having at least substantially the same fatigue characteristics as the blank after the step (i).

14. A method according to claim 11 further comprising the instrument after the step (iii) heat treat having at least substantially the same shape memory as the blank after the step (i).

15. A method according to claim 11 further comprising the instrument after the step (iii) heat treat having shape memory in a range of 60 to 75 percent after the instrument is subjected to a 90° bend and released.

16. A method of manufacturing an endodontic instrument from a nickel-titanium blank to obtain improved fatigue failure characteristics, the method comprising the steps of:
  (i) after cold working the nickel titanium blank, applying a heat treat in a temperature range of about 410 to 440° C.;
  (ii) after step (i), forming an instrument from the blank by performing machining operations; and
  (iii) after step (ii), heat treating the formed instrument in a range of 248 to 500° C.

* * * * *